United States Patent [19]

Hagedorn et al.

[11] Patent Number: 5,502,256

[45] Date of Patent: Mar. 26, 1996

[54] PROCESS FOR PREPARING 2,2'DINITRODIPHENYL DISULPHIDE

[75] Inventors: Ferdinand Hagedorn; Helmut Fiege; Robert Söllner, all of Leverkusen; Rudolf Helm, Bergisch Gladbach, all of Germany

[73] Assignee: Bayer Aktiengesellschaft, Leverkusen, Germany

[21] Appl. No.: 350,552

[22] Filed: Dec. 7, 1994

[30] Foreign Application Priority Data

Dec. 14, 1993 [DE] Germany ............ 43 42 619.0

[51] Int. Cl.$^6$ .................................................. C07C 323/09
[52] U.S. Cl. ............................................................ 568/25
[58] Field of Search ................................................. 568/25

[56] References Cited

U.S. PATENT DOCUMENTS 3,651,150   3/1972   Garrison et al. ............ 568/25

FOREIGN PATENT DOCUMENTS 0036120   9/1981   European Pat. Off. ........ 568/25
0156769   10/1985  European Pat. Off. ........ 568/25
0156769   10/1985  European Pat. Off. ........ 568/25
2204726   8/1972   Germany ..................... 568/25
1498410   1/1978   United Kingdom ........... 508/25

OTHER PUBLICATIONS

Helvetica Chimica Acta, "Zur Kenntnis der o–Aminobenzolsulfosaure (Orthanil–saure)", H. E. Fierz et al., pp. 663–668, 1929.

Gazzetta Chimica Italiana (5 Pages), vol. 110, Nos. 5–6, May–Jun. 1980; "The Synthesis of o–Nitrobenzenethiols: An . . . ", P. Battistoni et al.

Synthesis, International Journal of Methods in Synthetic Organic Chemistry, 1981, No. 8, 2 pages; "A Convenient Synthesis of Bis . . . ", M. Kodomari et al.

Chemical Abstracts, vol. 114, Feb. 4, 1991, No. 5, 3 pages; CA#42024p; "Synthesis of diallyl disulfide under phase––transfer . . . ", V. V. Nosyreva et al.

*Primary Examiner*—James H. Reamer
*Attorney, Agent, or Firm*—Sprung Horn Kramer & Woods

[57] ABSTRACT

2,2'-Dinitrodiphenyl disulphide is obtained in particularly good yields and purities in a simple manner by reacting 2-chloronitrobenzene with an aqueous alkali metal disulphide solution in the presence of phase transfer catalysts and an organic solvent.

11 Claims, No Drawings

PROCESS FOR PREPARING 2,2' DINITRODIPHENYL DISULPHIDE

The present invention relates to a process for preparing 2,2'-dinitrodiphenyl disulphide by reaction of 2-chloronitrobenzene with an aqeous alkali metal disulphide solution, which gives a purer product than in known processes in very good yields.

The preparation of 2,2'-dinitrodiphenyl disulphide from 2-chloronitrobenzene and sodium disulphide is described many times in the literature, with different reaction media being specified for the reaction, for example alcohols (Helv. Chim. Acta 663 [1929]) or dimethylformamide, N-methylpyrrolidinone and N-methylcaprolactam (German Offenlegungsschrift 2 204 726). The yields when using alcohols as solvent are generally moderate (68–86% of theory). Although the abovementioned cyclic and open-chain carboxylic acid-amides give yields of up to 94%, these special solvents are so valuable that, when used in the amounts described, they have to be separated off in a technically complicated manner and be processed for reuse.

The use of phase transfer catalysts as described in GB Patent Specification 1 498 410 gives yields of only barely 85%. EP-A 156 769 describes the reaction of 2-chloronitrobenzene with sodiumdisulphide in water and in the presence of a nonionic and/or an anionic surfactant. The amount of surfactant required here is relatively large, and large amounts of scrubbing agents (water or solvent) are required to remove the surfactant from the reaction product. In addition, in this method of operating, lumps and viscous masses are formed during the reaction, which lumps and masses are only handleable using special stirring devices, e.g. a dismembrator. The 2-chloronitrobenzene contained in these lumps and viscous masses only reacts very slowly to complete conversion. The 2,2,'-dinitrodiphenyl disulphide isolated after this reaction additionally contains by-products (according to Example 1 of EP-A 156 769, the product has a melting point of 182°–184° C. instead of 196° C. as given in the literature; according to Example 2, the product contains about 5% of by-products).

It was therefore an object of the invention to find an improved preparative process for 2,2'-dinitrodiphenyl disulphide, which gives a product having a high purity in good yield and in which no difficult-to-stir, viscous masses or lumps are formed during the reaction.

A process has now been found for preparing 2,2'-dinitrodiphenyl disulphide by reaction of 2-chloronitrobenzene with an aqueous alkali metal disulphide solution in the presence of phase transfer catalysts, which is characterized in that the reaction is carried out in the additional presence of an organic solvent.

Suitable phase transfer catalysts are, for example, quaternary ammonium and phosphonium salts of the formulae (I) and (II)

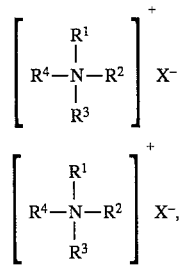

in which

R$^1$ to R$^4$ are identical or different and each represent a C$_1$–C$_{16}$-alkyl group, which can optionally be substituted by a hydroxy group, a C$_6$–C$_{10}$-aryl group, a C$_7$–C$_{11}$-aralkyl group or a C$_5$–C$_7$-cycloalkyl group, where two of the radicals R$^1$ to R$^4$ can together also form a ring having from 5 to 7 carbon atoms and X represents a halogen, a bisulphate radical or a hydroxy group.

Preferably, R$^1$ to R$^4$ are identical or different and each represent methyl, ethyl, n-propyl, i-propyl, n-butyl, i-butyl, t-butyl or benzyl. X preferably represents chlorine or bromine.

Particularly preferred phase transfer catalysts are tetra-n-butylammoniumbromide and benzyltriethylammonium chloride, which are particularly readily obtainable.

The phase transfer catalyst can be used, for example, in an amount of from 0.001 to 0.2 molar equivalents, based on 2-chloronitrobenzene. This amount is preferably from 0.01 to 0.1 molar equivalents.

Suitable organic solvents are, for example, dipolar, aprotic solvents. Preference is given to N-methylpyrrolidinone, N-methylcaprolactam, dimethylformamide and dimethylacetamide.

Dipolar, aprotic solvents can, for example, be used in amounts of from 10 to 20% by weight, based on 2-chloronitrobenzene. Recovery and reprocessing is then generally no longer required for economic reasons.

Suitable organic solvents also include, for example, alcohols. Preference is given to aliphatic alcohols and ether alcohols having from 1 to 8 carbon atoms. Particular preference is given to methanol, ethanol, isopropanol and isopropanol/water mixtures containing, for example, from 50 to 95% by weight of isopropanol.

Suitable organic solvents also include, for example, water-miscible ketones, in particular acetone.

Alcohols and water-miscible ketones which can be used for the purposes of the present invention have, at room temperature, a poor solvent capacity for the 2,2'-dinitrodiphenyl disulphide to be prepared; in contrast, they dissolve 2-chloronitrobenzene very readily. These solvents are readily miscible with water and, in the workup and isolation of the final product, they do not hinder the scrubbing out of the salt formed in the reaction.

Alcohols and water-miscible ketones can be used, for example, in such amounts that good stirrability of the reaction mixture is ensured. This amount can therefore be varied within wide limits. Frequently only from 50 to 100% by weight, based on 2-chloronitrobenzene, are required to achieve good stirrability. This gives a good space-time yield.

According to the invention, the process can be carried out, for example, by initially charging 2-chloronitrobenzene in the selected solvent with the phase transfer catalyst, heating this mixture while stirring to the desired reaction temperature and then adding the alkali metal disulphide solution dropwise.

In a particular embodiment of the process of the invention, only a fraction, for example from 5 to 20% by weight, of the 2-chloronitrobenzene to be reacted is initially charged with the organic solvent and the phase transfer catalyst and the main amount of the 2-chloronitrobenzene and the alkali metal sulphide solution are then metered simultaneously but separately from one another into the reaction mixture.

The duration of the addition of the reactants essentially depends on the technical opportunities for conducting away the heat of reaction. With a duration of from 2 to 4 hours for the addition, and of from 1 to 4 hours for the further reaction, yields of up to 98% of theory can be achieved.

The process of the invention is usually carried out under atmospheric pressure. In principle, it is also possible to carry out the process under increased pressure without deleterious effects on the result.

When using alcohols or water-miscible ketones, the reaction temperature can be, for example, between 20° C. and the boiling point of the solvent at atmospheric pressure. The reaction is advantageously carried out in a boiling solvent, since then the boiling under reflux can be utilized to conduct away the heat of reaction. With dipolar, aprotic solvents, the reaction temperature can be, for example, between 20° and 100° C.

2-Chloronitrobenzene and alkali metal disulphide can, for example, be used in a molar ratio of from 1.7 to 3:1. This ratio is preferably from 1.8 to 2.0:1.

The aqueous alkali metal disulphide solution can be used, for example, at a concentration of from 2 to 4 mol of alkali metal disulphide per liter of solution, preferably from 2.7 to 3.3 mol/l. The solution can also be added in a heated state.

The workup of the reaction mixture can, for example, be carried out by, after cooling the mixture to room temperature, separating off the crude, crystalline reaction product from the mother liquor by filtration, filtration with suction or centrifugation, freeing it of remaining salt by washing with water and, if necessary, purifying it further by washing with a cooled alcohol, e.g. methanol or isopropanol. The final product is preferably isolated and stored in a form moist with water, since in dried form it can, under certain circumstances, tend to dust explosions. 2,2'-Dinitrodiphenyl disulphide is an intermediate for the preparation of dyes, crop protection agents, pharmaceuticals and rubber chemicals.

The process of the invention has the surprising advantages that the reaction can be carried out substantially more selectively, more quickly, without the formation of agglomerates causing stirring difficulties and with high yields.

The process of the invention gives 2,2'-dinitrodiphenyl disulphide generally in yields between 94 and 98% and in purities of from 98.5 to 99.5%.

The following examples illustrate the process of the invention.

EXAMPLES

EXAMPLE 1

98.5 g of 2-chloronitrobenzene, 156 ml of N-methylpyrrolidinone and 20.0 g of tetra-n-butylammonium bromide were initially charged into a sulphiding beaker and heated while stirring to 90° C. At this temperature, a) a solution of 416.3 g of sodium sulphide ($Na_2S \cdot 3H_2O$) and 102.5 g of sulphur in 1175 ml of water and b) 886.3 g of melted 2-chloronitrobenzene were metered into the reaction mixture simultaneously but separately from one another over a period of 2 hours.

After the addition was complete, the mixture was stirred further for one hour at 90° C., cooled to room temperature and crude 2,2'-dinitrodiphenyl disulphide was separated off by filtration. The yellow substance was washed on the filter with water until free of chloride. This gave, after drying, 961.5 g of 2,2'-dinitrodiphenyl disulphide with a purity of 98.4% by weight (according to HPLC analysis), which corresponded to a yield of 98.2% of theory. Washing of the product on the filter with cold isopropanol and water enabled its purity to be increased to over 99.5% by weight.

EXAMPLE 2

225 g of 2-chloronitrobenzene, 166 g of a mixture of 85% by weight of isopropanol and 15% by weight of water and 3.2 g of tetra-n-butylammonium bromide were initially charged into a stirred flask and then heated while stirring to 70° C. At this temperature, 250 ml of a solution of 99.8 g of sodium sulphide ($Na_2S \cdot 3H_2O$), 25.0 g of sulphur and 180 ml of water were added dropwise over a period of 4 hours. The mixture was finally stirred further for 4 hours at 80° C., then cooled to 70° C. and crude 2,2'-dinitrodiphenyl disulphide was separated off by filtration. The yellow product was washed on the suction filter with isopropanol and water until free of chloride. This gave, after drying, 205.2 g of a product having a purity of 99.5% by weight, which corresponded to a yield of 93% of theory.

In a comparative experiment corresponding to Example 2, which was carried out in the absence of tetra-n-butylammonium bromide, 202.9 g of 2,2'-dinitrodiphenyl disulphide having a purity of 97% by weight were obtained. The yield was 89% of theory. The product was no longer suitable for use as an intermediate because of excessive contamination by by-products which could not be separated off.

EXAMPLE 3

The procedure of Example 2 was repeated, but using 166 g of methanol as solvent and 4.8 g of tetra-n-butylammonium bromide and 250 ml of a sodium disulphide solution which had been prepared from 99.8 g of $Na_2S \cdot 3H_2O$, 25 g of sulphur and 180 ml of water. The addition was carried out over a period of 3.5 hours and was in accordance with the procedure of Example 2. 205.9 g of 2,2'-dinitrodiphenyl disulphide having a purity of over 99.5% were obtained in a yield of 93% of theory.

What is claimed is:

1. A process for preparing 2,2'-dinitrodiphenyl disulphide which comprises reacting 2-chloronitrobenzene with aqueous alkali metal disulphide solution in the presence of 0.001 to 0.2 molar equivalents based on the amount of 2-chloronitrobenzene of a phase transfer catalyst and an organic solvent wherein the molar ratio of 2-chloronitrobenzene to alkali metal disulphide is from 1.7 to 3:1 and the organic solvent is selected from the group consisting of an alcohol, a water-miscible ketone, or a dipolar, aprotic solvent.

2. The process of claim 1, in which a quaternary ammonium or phosphonium salt is used as phase transfer catalyst.

3. The process claim 1, in which from 0.001 to 0.2 molar equivalent of phase transfer catalyst, based on 2-chloronitrobenzene, is used.

4. The process of claim 1, in which a dipolar, aprotic solvent is used in an amount of from 10 to 20% by weight, based on 2-chloronitrobenzene.

5. The process of claim 1, in which alcohol or a water-miscible ketone is used in an amount of from 50 to 100% by weight, based on 2-chloronitrobenzene.

6. The process of claim 1, in which an alcohol or a water-miscible ketone is used and the reaction is carried out at a temperature in the range from 20° C. to the boiling point of the solvent at atmospheric pressure.

7. The process of claim 1, in which a dipolar, aprotic solvent is used and the reaction is carried out at a temperature between 20° and 100° C.

8. The process of claims 1, in which 2-chloronitrobenzene, solvent and phase transfer catalyst are initially charged, this mixture is heated while stirring to the desired temperature and the alkali metal disulphide solution is then added dropwise.

9. The process of claim 1, in which from 5 to 20% by weight of the 2-chloronitrobenzene to be reacted are initially charged together with the organic solvent and the phase transfer catalyst, and the remaining amount of 2-chloronitrobenzene and the alkali metal sulphide solution are then metered in simultaneously but separately from one another.

10. The process of claim 1, in which 2-chloronitrobenzene and alkali metal disulphide are used in a molar ratio of from 1.7 to 3:1.

11. The process of claim 1, in which the aqueous alkali metal sulphide solution is used in a concentration of from 2 to 4 mol per liter of solution.

* * * * *